US00PP20835P2

(12) United States Plant Patent
Dümmen

(10) Patent No.: US PP20,835 P2
(45) Date of Patent: Mar. 16, 2010

(54) ***CALIBRACHOA* PLANT NAMED 'DUEALPUR'**

(50) Latin Name: ***Calibrachoa* sp.**
Varietal Denomination: Duealpur

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 0 days.

(21) Appl. No.: 12/313,676

(22) Filed: Nov. 21, 2008

(51) Int. Cl.
*A01H 5/00* (2006.01)

(52) U.S. Cl. ..... Plt./413

(58) Field of Classification Search ..... Plt./413

See application file for complete search history.

(56) References Cited

U.S. PATENT DOCUMENTS

PP15,427 P2 * 12/2004 Pierce ..... Plt./413

OTHER PUBLICATIONS

PlantScope Productrapport. "*Calibrachoa* 'Duealpur' Aloha Purple" available at: http://www.plantscope.nl/pls/pscprdpub/psc_htm_psc1521.pdtrapport?pnPdtId=238555&pnTalId=0&pcTerug=N.*

UPOV ROM GTITM Computer Database, GTI Jouve Retrieval Software 2009/03 Citation for 'Duealpur'.*

* cited by examiner

*Primary Examiner*—Wendy C Haas
(74) *Attorney, Agent, or Firm*—C. A. Whealy

(57) ABSTRACT

A new and distinct cultivar of *Calibrachoa* plant named 'Duealpur', characterized by its upright and outwardly spreading to trailing and decumbent plant habit; numerous large dark violet-colored flowers; and good garden performance.

1 Drawing Sheet

Botanical designation: *Calibrachoa* sp.
Cultivar denomination: 'Duealpur'.

BACKGROUND OF THE INVENTION

The present invention relates to a new and distinct cultivar of *Calibrachoa* plant, botanically known as *Calibrachoa* sp. and hereinafter referred to by the name 'Duealpur'.

The new *Calibrachoa* plant is a product of a planned breeding program conducted by the Inventor in Rheinberg, Germany. The objective of the breeding program is to create new *Calibrachoa* cultivars with large attractive flowers.

The new *Calibrachoa* originated from a cross-pollination made by the Inventor in August, 2005 in Rheinberg, Germany of a proprietary selection of *Calibrachoa* sp. identified as code number A04-0037-004, not patented, as the female, or seed, parent with a proprietary selection of *Calibrachoa* sp. identified as code number A04-0025-003, not patented, as the male, or pollen, parent. The new *Calibrachoa* was discovered and selected by the Inventor as a single flowering plant from within the progeny of the stated cross-pollination in a controlled greenhouse environment in Rheinberg, Germany in May, 2007.

Asexual reproduction of the new *Calibrachoa* plant by vegetative terminal cuttings in a controlled greenhouse environment in Rheinberg, Germany since May, 2007, has shown that the unique features of this new *Calibrachoa* plant are stable and reproduced true to type in successive generations.

SUMMARY OF THE INVENTION

Plants of the new *Calibrachoa* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duealpur'. These characteristics in combination distinguish 'Duealpur' as a new and distinct cultivar of *Calibrachoa:*

1. Upright and outwardly spreading to trailing and decumbent plant habit.
2. Numerous large dark violet-colored flowers.
3. Good garden performance.

The new *Calibrachoa* can be compared to plants of the female parent selection. Plants of the new *Calibrachoa* differ primarily from plants of the female parent selection in growth habit as plants of the new *Calibrachoa* are more vigorous than plants of the female parent selection.

The new *Calibrachoa* can be compared to plants of the male parent selection. Plants of the new *Calibrachoa* differ primarily from plants of the male parent selection in the following characteristics:

1. Plants of the new *Calibrachoa* are more vigorous than plants of the male parent selection.
2. Plants of the new *Calibrachoa* and the male parent selection differ in flower color as plants of the male parent selection have lavender-colored flowers.

Plants of the new *Calibrachoa* can be compared to plants of *Calibrachoa* 'Cal Pur', disclosed in U.S. Plant Pat. No. 15,427. Plants of the new *Calibrachoa* differ from plants of 'Cal Pur' in the following characteristics:

1. Plants of the new *Calibrachoa* have smaller leaves than plants of 'Cal Pur'.
2. Flowers of plants of the new *Calibrachoa* have longer petal lobes than flowers of plants of 'Cal Pur'.
3. Plants of the new *Calibrachoa* and 'Cal Pur' differ in flower color as plants of 'Cal Pur' have purple violet-colored flowers.

BRIEF DESCRIPTION OF THE PHOTOGRAPH

The accompanying colored photograph illustrates the overall appearance of the new *Calibrachoa*, showing the colors as true as it is reasonably possible to obtain in colored reproductions of this type. Colors in the photograph may differ slightly from the color values cited in the detailed botanical description which accurately describe the colors of the new *Calibrachoa*. The photograph is a top perspective view of a typical flowering lateral branch of 'Duealpur'.

DETAILED BOTANICAL DESCRIPTION

The aforementioned photograph and following observations, measurements and values describe plants grown in Rheinberg, Germany, under commercial practice during the spring in a glass-covered greenhouse with day and night temperatures averaging 18° C. and light levels averaging 4,500 lux. Rooted young plants were pinched one time about three weeks after planting had been growing for 16 weeks when the photograph and description were taken. In the following description, color references are made to The Royal Horticultural Society Colour Chart, 1995 Edition, except where general terms of ordinary dictionary significance are used.

Botanical classification: *Calibrachoa* sp. 'Duealpur'.

Parentage:

*Female, or seed, parent.*—Proprietary selection of *Calibrachoa* sp. identified as code number A04-0037-004, not patented.

*Male, or pollen, parent.*—Proprietary selection of *Calibrachoa* sp. identified as code number A04-0025-003, not patented.

Propagation:

*Type.*—By vegetative cuttings.

*Time to initiate roots, summer.*—About seven days at 20° C.

*Time to initiate roots, winter.*—About ten days at 20° C.

*Time to produce a rooted young plant, summer.*—About three weeks at temperatures of 20° C.

*Time to produce a rooted young plant, winter.*—About four weeks at temperatures of 20° C.

*Root description.*—Fine, fibrous; white in color.

*Rooting habit.*—Freely branching; dense.

Plant description:

*Plant and growth habit.*—Upright and outwardly spreading to trailing and decumbent plant habit. Freely branching habit with about 10 to 15 lateral branches; pinching enhances branching; vigorous growth habit.

*Plant height.*—About 11.5 cm.

*Plant diameter.*—About 22 cm.

Lateral branch description:

*Length.*—About 11 cm.

*Diameter.*—About 1.5 mm.

*Internode length.*—About 1.2 cm.

*Strength.*—Strong.

*Aspect.*—Initially upright to outwardly spreading to trailing and decumbent.

*Texture.*—Pubescent.

*Color.*—Close to 144B.

Foliage description:

*Arrangement.*—Before flowering, alternate, simple; after flowering, opposite, simple.

*Length.*—About 2.6 cm.

*Width.*—About 8 mm.

*Shape.*—Oblanceolate.

*Apex.*—Rounded.

*Base.*—Cuneate.

*Margin.*—Entire.

*Texture, upper and lower surfaces.*—Pubescent.

*Venation pattern.*—Pinnate; arcuate.

*Color.*—Developing and fully expanded leaves, upper surface: Close to 137C; venation, close to 144C. Developing and fully expanded leaves, lower surface: Close to 138B to 138C; venation, close to 144C.

*Petiole.*—Length: About 2 mm. Diameter: About 1 mm. Texture, upper and lower surfaces: Pubescent. Color, upper and lower surfaces: Close to 144B.

Flower description:

*Flower arrangement and habit.*—Single salverform flowers arising from leaf axils. Freely flowering habit with usually about 40 open flowers and flower buds per plant. Flowers face upright or outwardly.

*Fragrance.*—None detected.

*Natural flowering season.*—Plants of the new *Calibrachoa* initiate and develop flowers about four to ten weeks after planting. Plants flower continuously from the spring until the autumn in Germany.

*Flower longevity.*—Individual flowers last about seven to ten days on the plant; flowers not persistent.

*Flower diameter.*—About 3.8 cm.

*Flower length* (*height*).—About 2.4 cm.

*Flower throat diameter.*—About 9 mm.

*Flower tube length.*—About 1.7 cm.

*Flower tube diameter, base.*—About 2 mm.

*Flower bud.*—Shape: Elongated oblong. Length: About 2.4 cm. Diameter: About 5 mm. Color: Close to 145C tinted with close to 59A.

*Corolla.*—Arrangement: Five petals fused at the base and opening into a flared trumpet. Petal length from throat: About 1.8 cm. Petal lobe width: About 1.9 cm. Petal shape: Roughly spatulate. Petal apex: Shallowly cordate. Petal margin: Entire. Petal texture, upper and lower surfaces: Smooth, glabrous. Throat texture: Smooth, glabrous. Tube texture: Smooth, glabrous. Color: Petal, when opening, upper surface: Close to 83A to 83B. Petal, when opening, lower surface: Close to 83C. Petal, fully opened, upper surface: Close to 88B; venation, close to 59A to 59B; color becoming closer to 87A to 87B with development. Petal, fully opened, lower surface: Close to 88D; venation, close to 59A. Throat: Close to 7A; venation, close to 59A. Tube: Close to 151C; venation, close to 59A.

*Calyx.*—Arrangement: One star-shaped calyx tube with five sepals fused at the base. Sepal length: About 1.2 cm. Sepal width: About 3.2 mm. Sepal shape: Lanceolate. Sepal apex: Acute. Sepal margin: Entire. Sepal texture, upper and lower surfaces: Pubescent. Color, upper surface: Close to 137C. Color, lower surface: Close to 138A.

*Peduncles.*—Length: About 1.9 cm. Diameter: About 1 mm. Angle: About 45° from stem axis. Strength: Moderately strong. Texture: Pubescent. Color: Close to 144B.

*Reproductive organs.*—Stamens: Quantity/arrangement: Five per flower. Filament length: About 8 mm. Filament color: Close to 145C. Anther shape: Ellipsoidal. Anther length: About 1.5 mm. Anther color: Close to 7B. Pollen amount: Scarce. Pollen color: Close to 13C. Pistils: Quantity: One per flower. Pistil length: About 1 cm. Style length: About 7 mm. Style color: Close to 144D. Stigmn shape: Ellipsoidal. Stigma color: Close to 144B. Ovary color: Close to 144D. Seed/fruit: Seed and fruit development have not been observed on plants of the new *Calibrachoa*.

Garden performance: Plants of the new *Calibrachoa* have been observed to have good garden performance and tolerate wind, rain and temperatures ranging from about 2° C. to about 38° C.

Pathogen/pest resistance: Plants of the new *Calibrachoa* have not been observed to be resistant to pathogens and pests common to *Calibrachoa*.

It is claimed:

1. A new and distinct *Calibrachoa* plant named 'Duealpur' as illustrated and described.

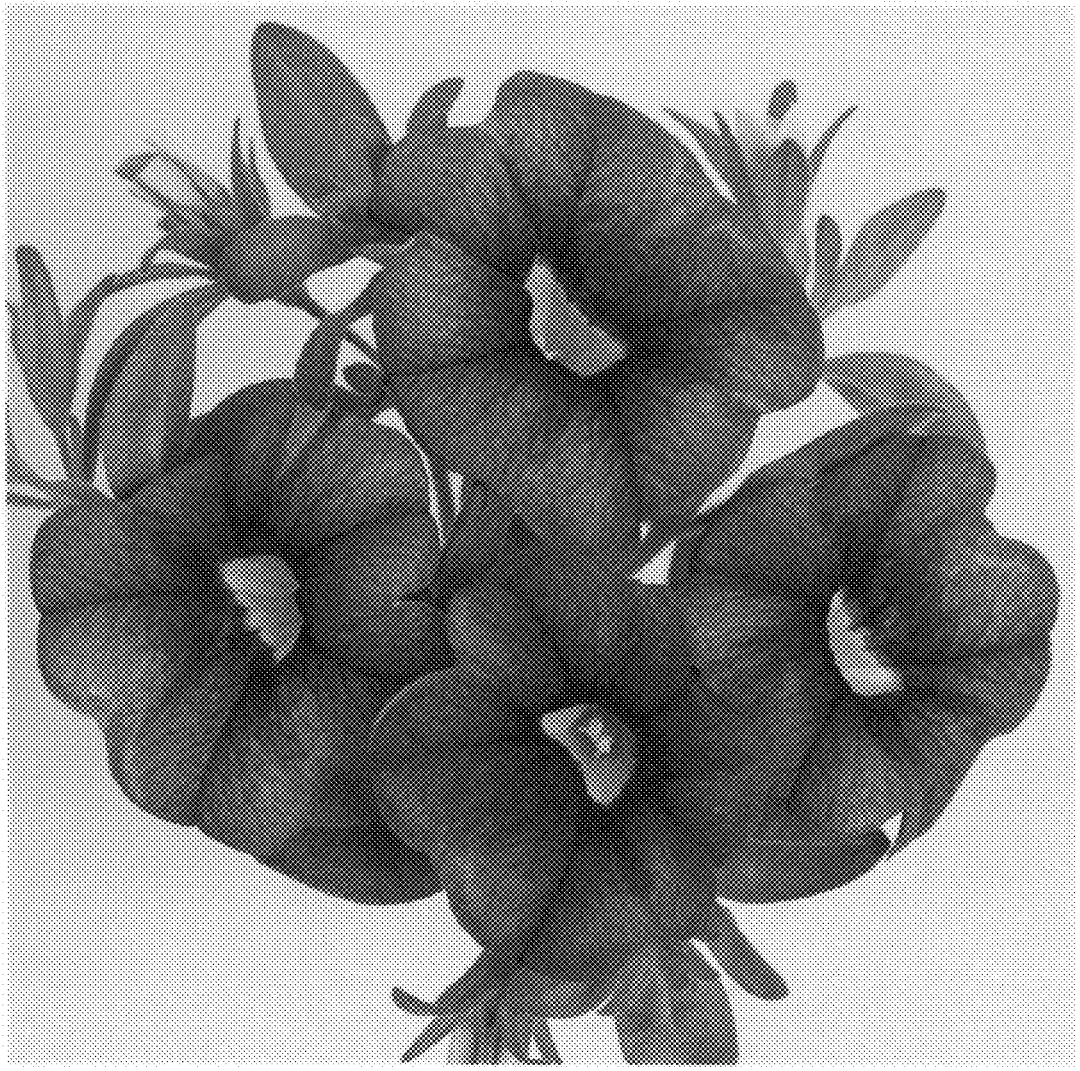

* * * * *